United States Patent
Samain et al.

(10) Patent No.: US 6,423,297 B1
(45) Date of Patent: Jul. 23, 2002

(54) AEROSOL DEVICE BASED ON ALCOHOL COMPOSITIONS OF FIXING MATERIALS COMPRISING ANIONIC GRAFTED SILICONE POLYMERS

(75) Inventors: Henri Samain, Bievres; Christine Dupuis, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/976,515

(22) Filed: Nov. 24, 1997

(30) Foreign Application Priority Data

Nov. 22, 1996 (FR) .............................. 96 14331

(51) Int. Cl.$^7$ .............................. A61L 9/04; A61K 7/06
(52) U.S. Cl. ................ 424/45; 424/70.1; 424/70.11; 424/70.12; 424/70.15; 424/70.16; 424/70.2
(58) Field of Search ................ 424/45, 70.1, 70.2, 424/70.11, 70.12, 70.15, 70.16

(56) References Cited

U.S. PATENT DOCUMENTS 5,468,477 A * 11/1995 Kumar et al. ............ 424/78.17

FOREIGN PATENT DOCUMENTS

| WO | WO 95/03776 | | 2/1995 |
| WO | WO 96/21417 | | 7/1996 |
| WO | 96/21417 | * | 7/1996 |
| WO | WO 96/32918 | | 10/1996 |
| WO | 96/32918 | * | 10/1996 |

\* cited by examiner

*Primary Examiner*—Thurman K. Page
*Assistant Examiner*—Lakshmi Channavajjala
(74) *Attorney, Agent, or Firm*—Finnegan, Henderson, Farabow, Garrett & Dunner, L.L.P.

(57) ABSTRACT

An aerosol device comprising a container containing an aerosol composition comprising a liquid phase (or fluid) containing at least one fixing material in a suitable solvent, a propellant, and a means for distributing the aerosol composition, the fixing material having a glass transition temperature (Tg) of greater than or equal to 30° C., the fixing material comprising at least one anionic grafted silicone polymer having a polysiloxane skeleton grafted with at least one anionic hydrocarbon radical, and the device being suitable for obtaining a wetting power of greater than or equal to 30 mg/s. The invention also relates to a process for treating keratin fibers, in which a composition comprising a fixing material having a glass transition temperature (Tg) of greater than or equal to 30° C., this fixing material comprising at least one anionic grafted silicone polymer, is applied to the fibers by means of a suitable device in order to obtain a wetting power of greater than or equal to 30 mg/s.

18 Claims, No Drawings

AEROSOL DEVICE BASED ON ALCOHOL COMPOSITIONS OF FIXING MATERIALS COMPRISING ANIONIC GRAFTED SILICONE POLYMERS

The present invention relates to novel aerosol devices intended to fix the hair.

The hair products, for shaping and/or holding the hairstyle which are the most widely available on the cosmetics market are spray compositions comprising a solution, usually an alcoholic or aqueous solution, and one or more materials, generally polymer resins, whose function it is to form welds between the individual strands of hair, these materials also being known as fixing materials, mixed with various cosmetic adjuvants. These solutions are generally packaged either in a suitable aerosol container placed under pressure with the aid of a propellant or in a pump-dispenser bottle.

Many aerosol systems intended to fix the hair are known; these systems containing, on the one hand, a liquid phase (or fluid) and, on the other hand, a propellant. The liquid phase contains the fixing materials and a suitable solvent. The function of the propellant is to provide a pressure which allows the liquid phase to be sprayed and to be applied to the hair in the form of a cloud of dispersed droplets. It is after the liquid phase has been applied to the hair that it dries, allowing the formation of welds which are necessary for fixing the hair, by means of the fixing materials.

It is desired that the welds be rigid enough to ensure that the hair is held in place. However, it is also desired that they be fragile enough for the user to be able to destroy them by combing or brushing the hair, without damaging the scalp or the hair.

The fixing materials are generally fixing polymers, that is to say film-forming polymers that are soluble or dispersible in water and/or in alcohol, such as vinyl acetate/crotonic acid copolymers and anionic or amphoteric acrylic resins. These materials make it possible readily to obtain the fixing effect but, on the other hand, after brushing or combing, under the usual conditions of lacquering, the hair looks stiff and has a coarse or even sticky feel and is often difficult to disentangle.

These drawbacks are linked to several parameters, among which mention may be made of the nature of the fixing polymer(s), or alternatively the nature of the welds. To overcome these drawbacks, it is desirable to act on these two parameters without, however, diminishing the desired fixing effect. To improve the cosmetic properties of fixing materials, it has been proposed to combine different polymers, for example in the documents, WO 94/12148, WO 96/06592 and U.S. Pat. No. 5,158,762, the disclosures of which are specifically incorporated by reference herein.

The inventors have found that by appropriately selecting, on the one hand, the fixing polymers and, on the other hand, the diffusion parameters for the compositions, it is possible to act on the quality of the welds while at the same time retaining good fixing and/or hair shaping qualities, and thus to provide excellent cosmetic properties such as softness, disentangling and feel.

The aerosol device according to the invention comprises a container containing an aerosol composition comprising, on the one hand, a liquid phase (or fluid) containing at least one fixing material in a suitable solvent and, on the other hand, a propellant, and a means for distributing the aerosol composition, the fixing material having a glass transition temperature (Tg) of greater than or equal to 30° C., the fixing material comprising at least one anionic grafted silicone polymer having a polysiloxane skeleton grafted with at least one anionic hydrocarbon radical, and the device being suitable for obtaining a wetting power of greater than or equal to 30 mg/s.

The distribution means generally comprises a distribution valve controlled by a distribution head, itself comprising a nozzle through which the aerosol composition is vaporized.

The terms "Tg" and "wetting power" as understood according to the present invention are defined below.

According to the present invention, the expression glass transition temperature (Tg) is understood to refer to the Tg of the fixing material in the dry extract, the dry extract comprising all of the non-volatile materials in the fluid, or solids.

According to the present invention, the wetting power corresponds to the amount of product received by a sheet of plastic placed 35 cm away from the nozzle of the aerosol device over a given unit of time. The product then comprises the solids plus some of the solvent which has not evaporated over the trajectory plus, possibly, some of the non-evaporated propellant. This wetting power is expressed in mg/s and is measured according to the invention by the following method:

a sheet of plastic 21 cm×23 cm in size is suspended vertically on a precision balance (1/1000), the sheet being connected to the balance via the upper edge (generally by means of a balance hook inserted into a perforation placed at the center of the width and 1 cm from the upper edge of the sheet), and is kept vertical by applying a weight centered on the lower edge (generally by means of a clip fixed to and centered on the lower edge);

a block is placed behind the lower edge of the sheet in order to keep the sheet vertical during impacting of the product;

the aerosol device is placed vertically such that the composition diffusion nozzle is arranged at the center and 35 cm away from the vertical sheet, to allow vaporization of the product perpendicular to the sheet;

the composition is vaporized for 5 seconds; and the amount of product received on the vertical sheet is measured once the vaporization is complete.

For greater precision, a suitable device comprising a support means for the aerosol device and means for allowing three-dimensional adjustment of the position of the nozzle relative to the vertical sheet may be used. This device may also be equipped with a pneumatic spray-control (firing and duration) device, so as to control the duration of the vaporization precisely. The whole assembly may be controlled by computer.

To avoid any environmental interference, the trajectory of the product between the nozzle and the sheet will advantageously be protected horizontally and vertically by the walls of a tunnel of suitable size.

Lastly, the product is advantageously vaporized under a controlled atmosphere, preferably at a temperature of 20° C. and at a relative humidity of 30%.

Preferably, the fixing material has a Tg of greater than or equal to 60° C.

Advantageously, the fixing material comprises the anionic grafted silicone polymer, alone or in combination with common cosmetic additives, for example plasticizers or neutralizing agents.

According to the present invention, and in accordance with general acceptance within the cosmetics art, the term silicone polymer is understood to denote any organosilicon polymer or oligomer with a linear or cyclic, branched or crosslinked structure, of variable molecular weight, obtained by polymerization and/or polycondensation of suitably functionalized silanes, and comprising a repetition of main units in which the silicon atoms are connected together by oxygen atoms (siloxane bond ≡Si—O—Si≡), optionally substituted hydrocarbon radicals being linked directly via a carbon atom onto the silicon atoms. The most common hydrocarbon radicals are alkyl radicals, especially $C_1$–$C_{10}$ alkyl radicals and, in particular, methyl, fluoroalkyl radicals, aryl radicals and in particular phenyl, and alkenyl radicals and in particular vinyl; other types of radicals which may be linked, either directly or via an anionic hydrocarbon radical intermediate, to the siloxane chain are especially hydrogen, halogens and in particular chlorine, bromine or fluorine, thiols, alkoxy radicals, polyoxyalkylene radicals (or polyethers) and in particular polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, this list obviously not being limiting in any way, and clearly including so-called "organomodified" silicones.

According to the present invention, the term hydrocarbon radical is understood to refer to a non-silicone hydrocarbon radical.

The anionic silicone polymers which are useful according to the present invention are those which comprise a main silicone chain (or polysiloxane (≡Si—O—)$_n$) onto which at least one non-silicone anionic hydrocarbon radical is grafted, within the chain as well as, optionally, on at least one of its ends. The anionic hydrocarbon radical is preferably an anionic hydrocarbon polymer. The anionic charges may be provided by at least one ionizable function, in particular by at least one carboxylic acid or sulphonic acid function, and their addition salts with a base, for example sodium hydroxide, potassium hydroxide, 2-amino-2-methyl-1-propanol, monoethanolamine, triethanolamine, triisopropanolamine, or aqueous ammonia, etc.

Preferably, the number-average molecular mass of the anionic grafted silicone polymers according to the invention is greater than approximately 5000, preferably approximately ranging from 10,000 to 1,000,000, and more preferably approximately from 10,000 to 100,000.

The silicone chain/anionic hydrocarbon radical weight ratio ranges preferably from 5195 to 40/60.

Lastly, the anionic grafted silicone polymers according to the invention are advantageously rapidly-rigidifying polymers. According to the invention, the expression rapidly-rigidifying polymers is understood to refer to polymers which lead to rigid welds in less than 10 minutes.

The anionic grafted silicone polymers which are useful according to the invention may be existing commercial products or alternatively may be obtained according to any means known to those skilled in the art, in particular by reaction between (i) a starting silicone which is correctly functionalized on one or more of these silicon atoms and (ii) a non-silicone organic compound which is itself correctly functionalized by a function which is capable of reacting with the functional group(s) borne by the silicone, forming a covalent bond. A standard example of such a reaction is the hydrosilylation reaction between ≡Si—H groups and vinyl groups $CH_2$=CH—, or alternatively the reaction between thio-functional groups —SH with these same vinyl groups.

Examples of anionic grafted silicone polymers which are suitable for carrying out the present invention, as well as their specific mode of preparation, are described in particular in European patent application EP-A-0,582,152, and International patent applications WO 93/23009 and WO 95/03776, the teachings of which are included in the present description in their entirety by way of non-limiting references.

According to a particularly preferred embodiment of the present invention, the anionic grafted silicone polymer used comprises the result of the radical copolymerization between, on the one hand, at least one non-silicone anionic organic monomer having ethylenic unsaturation and/or a non-silicone hydrophobic organic monomer having ethylenic unsaturation and, on the other hand, a silicone having in its chain at least one functional group which is capable of reacting with the ethylenic unsaturations of the non-silicone monomers, forming a covalent bond, in particular thio-functional groups.

According to the present invention, the anionic monomers containing ethylenic unsaturation are preferably chosen, alone or as a mixture, from linear or branched, unsaturated carboxylic acids which are optionally partially or totally neutralized in the form of a salt, it being possible for this or these carboxylic acids to be, more particularly, acrylic acid, methacrylic acid, maleic acid, maleic anhydride, itaconic acid, fumaric acid or crotonic acid. The suitable salts are, in particular, alkali-metal, alkaline-earth metal and ammonium salts. Similarly, it will be noted that, in the final anionic grafted silicone polymer, the organic group of anionic nature which comprises the result of the radical (homo) polymerization of at least one anionic monomer of unsaturated carboxylic acid type may be, after reaction, post-neutralized with a base, such as sodium hydroxide, potassium hydroxide, aqueous ammonia, etc., in order to bring it into the form of a salt.

According to the present invention, the hydrophobic monomers containing ethylenic unsaturation are preferably chosen, alone or as a mixture, from alkanol esters of acrylic acid and/or alkanol esters of methacrylic acid. The alkanols are preferably $C_1$–$C_{18}$ alkanols, and more preferably $C_1$–$C_{12}$ alkanols. The preferred monomers are chosen from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate, stearyl (meth)acrylate or mixtures thereof.

One family of anionic grafted silicone polymers which is particularly suitable for carrying out the present invention comprises silicone polymers containing in their structure the unit of formula (I) below:

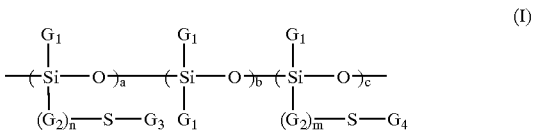

in which the radicals $G_1$, which may be identical or different, represent hydrogen or a $C_1$–$C_{10}$ alkyl radical, or alternatively a phenyl radical; the radicals $G_2$, which may be identical or different, represent a $C_1$–$C_{10}$ alkylene group; $G_3$ represents a polymer residue resulting from the (homo) polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 30; b is an integer ranging from 10 to 330; and c is an integer ranging from 0 to 30; with the proviso that one of the parameters a and c is other than 0.

Preferably, the unit of formula (I) above has at least one, and even more preferably all, of the following characteristics:

- the radicals $G_1$ denote an alkyl radical, preferably a methyl radical;
- n is non-zero, and the radicals $G_2$ each represent a divalent $C_1$–$C_3$ radical, preferably a propylene radical;
- $G_3$ represents a polymeric radical resulting from the (homo)polymerization of at least one monomer of the carboxylic acid type containing ethylenic unsaturation, preferably acrylic acid and/or methacrylic acid;
- $G_4$ represents a polymer radical resulting from the (homo) polymerization of at least one monomer of the ($C_1$–$C_{10}$)alkyl (meth)acrylate type, preferably of the isobutyl or methyl (meth)acrylate type.

Examples of silicone polymers corresponding to formula (I) are, in particular, polydimethylsiloxanes (PDMS) onto which are grafted, via a linking chain of thiopropylene type, mixed polymer units of the poly(meth)acrylic acid type and of the polymethyl (meth)acrylate type.

Other examples of silicone polymers corresponding to formula (I) are, in particular, polydimethylsiloxanes (PDMS) onto which are grafted, via a linking chain of thiopropylene type, polymer units of the polyisobutyl (meth) acrylate type.

Among the anionic grafted silicone polymers which are useful according to the invention, mention will be made more particularly of the product marketed under the name VS80 by the company [lacuna].

The fixing material may be used in dissolved form or in the form of dispersions of solid polymer particles.

The aerosol device according to the invention is advantageously suitable for obtaining a wetting power ranging from 30 mg/s to 300 mg/s.

According to a preferred embodiment of the invention, the aerosol device according to the invention is suitable for obtaining a solids flow rate of greater than or equal to 20 mg/s, preferably ranging from 20 to 60 mg/s.

According to the present invention, the solids flow rate ($D_{SM}$) corresponds to the amount of dry extract which leaves the aerosol device per unit of time. This solids flow rate is expressed in mg/s and is calculated by multiplying the solids concentration in the aerosol composition ($C_{SM}$) by the flow rate of the aerosol composition at the nozzle outlet ($D_{AC}$):

$$D_{SM}=C_{SM} \times D_{AC}.$$

The solids concentration in the aerosol composition ($C_{SM}$) corresponds to the amount of solids relative to 100 g of aerosol composition (fluid+propellant). The solids concentration is expressed as a percentage and is measured after spraying by evaporation of the volatile components of the spray residue for 1 hour 30 at 105° C.

The flow rate of aerosol composition ($D_{AC}$) corresponds to the amount of aerosol composition (fluid+propellant) leaving the aerosol device per unit of time. It is expressed in mg/s and is measured by the difference between the weight of aerosol before ($M_0$) and after ($M_1$) vaporization for 10 seconds:

$$D_{AC}=(M_0-M_1)/10.$$

The solids flow rate and wetting power characteristics of the aerosol devices according to the invention depend, on the one hand, on the aerosol composition and, on the other hand, on the means of distribution, the two needing to be suitable in order to obtain the desired characteristics. Among the parameters which may influence these characteristics, mention will be made more particularly of the solids concentration ($C_{SM}$), the flow rate of aerosol composition ($D_{AC}$) and the phase of the aerosol composition.

The solids concentration ($C_{SM}$) ranges advantageously from 2.5 to 15% by weight relative to the total weight of the aerosol composition (fluid+propellant), and preferably from 3.5 to 10% by weight.

The flow rate of aerosol composition ($D_{AC}$) will thus be suitable to obtain a flow rate of solids ($D_{SM}$) as defined above. The $D_{AC}$ will preferably range from 300 to 800 mg/s, more preferably will be close to 600 mg/s.

The phase of the aerosol composition is preferably a long phase, that is to say that the fluid/propellant weight ratio is greater than 1/1, and more preferably ranges from 1.2/1 to 3/1.

The appropriate solvent advantageously contains at least 30% by volume of alcohol, preferably at least 70% by volume of alcohol. According to the invention, the term alcohol is understood to refer to a $C_1$–$C_4$ aliphatic alcohol, preferably ethanol.

The propellant comprises the compressed or liquefied gases usually used for the preparation of aerosol compositions. Air, carbon dioxide or nitrogen, these being compressed, or a gas which is soluble or insoluble in the composition, such as dimethyl ether, fluoro or non-fluoro hydrocarbons, and mixtures thereof, will preferably be used.

The aerosol composition according to the invention may also comprise other fixing polymers provided that they do not alter the characteristics of the device according to the invention, in particular as regards the Tg value of the fixing material. These fixing polymers are, in particular, acrylic acid copolymers such as acrylic acid/ethyl acrylate/N-tert-butylacrylamide terpolymer (marketed in particular under the name Ultrahold Strong by the company BASF), or alternatively polymers containing vinyllactam units which are useful according to the invention, and mention can be made more particularly of polyvinylpyrrolidones, polyvinylcaprolactams, polyvinylpyrrolidone/vinyl acetate copolymers, polyvinylpyrrolidone/non-quaternized diaminoethyl methacrylate copolymers (marketed in particular under the names Copolymer 845, Copolymer 958 and Copolymer 937 by the company ISP), polyvinylpyrrolidone/vinyl acetate/vinyl propionate terpolymers (marketed in particular under the name Luviskol VAP 343 by the company BASF), vinylcaprolactam/vinylpyrrolidone/dimethylaminoethyl methacrylate terpolymers (marketed in particular under the names Gaffix VC 713, H₂OLD, ACP 1187 and ACP 1189 by the company ISP) and (meth)acrylic acid/(meth)acrylates/vinylpyrrolidone terpolymers (marketed in particular under the names Stepan-hold Extra by the company Stepan, Luvimer VBM 35 and Luvimer VBM 70 by the company BASF) or crotonic acid/vinyl acetate/vinyl t-butylbenzoate terpolymer. More particularly, the polymers containing vinyllactam units disclosed in the copending U.S. patent application entitled "Aerosol Device Based on Alcoholic Compositions of Fixing Materials Comprising Vinyllactam Units," filed the same day as the present application and in the name of the same inventors of the present application, the disclosure of which is specifically incorporated herein by reference, can be advantageously used in accordance with the present invention.

Depending on the aerosol composition (fluid+propellant), a person skilled in the art will know how to select the appropriate distribution means in order to obtain the desired flow rate of solids and wetting power characteristics.

The specific characteristics defined above, solids concentration ($C_{SM}$) and phase, may be obtained by selecting the appropriate distribution means and/or by modifying the formulation.

The appropriate valves for the above specific compositions are, in particular, straight-line valves with a spray nozzle having a diameter ranging from 0.35 to 0.60 mm, preferably from 0.40 to 0.30 mm, advantageously without internal restriction or an additional gas connection. These are, in particular, valves marketed under the name Coster T104 RA36/0/4 by the company Coster or the Precision Experimental 15130 valve comprising a spray nozzle and a valve body 0.46 mm in diameter without an additional gas connection, from the company Precision.

The appropriate diffusers for the above specific compositions are, in particular, push-buttons marketed under the name Precision 216903-40AD29 by the company Precision.

The present invention also relates to a process for treating keratin fibers, in which a composition comprising a fixing material having a glass transition temperature (Tg) of greater than or equal to 30° C., this fixing material comprising at least one anionic grafted silicone polymer as defined above, is applied to the fibers by means of a suitable device in order to obtain a wetting power of greater than or equal to 30 mg/s.

The examples below illustrate the invention without, however, limiting its scope. In the examples, "AM" means "active material".

EXAMPLE 1

Five fluids were prepared containing 5.7% by weight of fixing polymers in ethanol for the five fixing polymers below:

A—VS 80 (marketed by the company 3M), anionic grafted silicone polymer according to the invention,
B—terpolymer of methylsiloxane containing methylthio groups/dimethylaminoethyl methacrylate/isobutyl methacrylate (20/10/70), which is a cationic grafted silicone polymer outside the scope of the present invention,
C—dimethyl/methylsiloxane copolymer containing polyacrylic ester groups, which is a nonionic grafted silicone polymer outside the scope of the present invention,
D—acrylic acid/tert-butyl acrylate/methacrylate terpolymer containing grafted PDMS groups (20/60/20), described in patent application EP 412,704, and is outside the scope of the present invention, and
E—octylacrylamide/acrylates/butylaminoethyl methacrylate (CTFA) marketed under the name Amphomer by the company National Starch, and is outside the scope of the present invention.

Five aerosol devices 1 to 5 were prepared by introducing 65 g of compositions A to E respectively into separate aerosol cans. The five cans were fitted with a Precision Experimental 15130 valve and 35 g of dimethyl ether as propellant and a Precision 21690340AD29 push-button were then added.

The above five devices were each tested on locks of hair as follows:
a lock of about 5 g of washed and dried hair was prepared, the hair was spread out in a fan shape and the lock was suspended,
the composition was sprayed for 5 seconds on each side, and
the lock was allowed time to dry (about 10 minutes).

The performance of each device was then evaluated by a panel of eight experts who noted, in a blind study, the following parameters: lacquering power, quality of feel, visual quality and ease of disentangling. The performance levels were graded from 0 to 30, 0 corresponding to unacceptable performance levels, 30 to excellent performance levels.

The averages obtained for the five devices are given in the table below.

| Device | 1 | 2* | 3* | 4* | 5* |
|---|---|---|---|---|---|
| Polymer | A | B | C | D | E |
| Lacquering power | 35 | 15 | 15 | 35 | 35 |
| Feel | 32 | 5 | 5 | 17 | 17 |
| Visual aspect | 40 | 5 | 5 | 25 | 30 |
| Disentangling | 40 | 35 | 40 | 20 | 12 |

*Comparative

Only device 1 according to the invention obtained a satisfactory grade for the four criteria selected, the other four devices giving inferior results, both in regard to the lacquering power, the feel or the visual aspect (devices 2 and 3) and in regard to the ease of disentangling (devices 4 and 5).

EXAMPLE 2

| The following fluids were prepared: | |
|---|---|
| VS80 marketed by the company 3M | 3.0 g AM |
| Acrylic acid/ethyl acrylate/N-tert-butylacrylamide terpolymer marketed under the name Ultrahold Strong by the company BASF | 3.0 g AM |
| Ethanol qs | 100.00 g |

The aerosol device according to the invention was prepared by introducing 65 g of the above fluid into an aerosol can. The can was fitted with a Precision Experimental 15130 valve and 35 g of dimethyl ether as propellant and a Precision 216903-40AD29 push-button were then added.

This device according to the invention made it possible to obtain the cosmetic fixing, feel and disentangling results in accordance with the invention.

We claim:

1. An aerosol device, comprising:
a container containing an aerosol composition, said composition comprising a liquid phase containing at least one fixing material in a suitable solvent and a propellant, wherein said at least one fixing material has a glass transition temperature (Tg) of greater than or equal to 30° C. and comprises at least one anionic grafted silicone polymer, said polymer having a polysiloxane skeleton grafted with at least one anionic hydrocarbon radical; and
a means for distributing said aerosol composition, wherein said device provides a wetting power of greater than or equal to 30 mg/s.

2. A device according to claim 1, wherein said polymer comprises a main silicone chain or polysiloxane ($\equiv$Si—O—)$_n$ onto which at least one non-silicone anionic hydrocarbon radical is grafted, said grafting being within the chain and/or on the end of the chain.

3. A device according to claim 1, wherein said anionic hydrocarbon radical comprises at least one carboxylic or sulphonic acid function or a base addition salt thereof.

4. A device according to claim 1, wherein the silicone chain/anionic hydrocarbon group weight ratio ranges from 5/95 to 40/60.

5. A device according to claim 1, wherein said device provides a wetting power ranging from 30 mg/s to 300 mg/s.

6. A device according to claim 1, wherein said device provides a solids flow rate of greater than or equal to 20 mg/s.

7. A device according to claim 6, wherein said solids flow rate ranges from 20 to 60 mg/s.

8. A device according to claim 1, wherein the solids concentration ($C_{SM}$) ranges from 2.5 to 15% by weight relative to the total weight of the aerosol composition (liquid+propellant).

9. A device according to claim 8, wherein said solids concentration ($C_{SM}$) ranges from 3.5 to 10% by weight relative to the total weight of the aerosol composition (liquid+propellant).

10. A device according to claim 1, wherein the flow rate of said aerosol composition ($D_{AC}$) ranges from 300 to 800 mg/s.

11. A device according to claim 10, wherein the flow rate of said aerosol composition ($D_{AC}$) is approximately 600 mg/s.

12. A device according to claim 1, wherein the fluid/propellant weight ratio in said aerosol composition is greater than 1/1.

13. A device according to claim 12, wherein said fluid/propellant weight ratio in said aerosol composition ranges from 1.2/1 to 3/1.

14. A device according to claim 1, wherein said suitable solvent contains at least 30% by volume of alcohol.

15. A device according to claim 14, wherein said suitable solvent contains at least 70% by volume of alcohol.

16. A device according to claim 1, wherein said aerosol composition further comprises at least one additional fixing polymer.

17. A device according to claim 1, wherein said at least one anionic grafted silicone polymer is a rapidly-rigidifying polymer.

18. A process for treating keratin fibers, said process comprising applying to said fibers, by means of a suitable device that maintains a wetting power of greater than or equal to 30 mg/s, a composition comprising at least one fixing material having a glass transition temperature (Tg) of greater than or equal to 30° C., said fixing material comprising at least one anionic grafted silicone polymer, said polymer having a polysiloxane skeleton grafted with at least one anionic hydrocarbon radical.

* * * * *